US006969008B2

(12) United States Patent
Helf et al.

(10) Patent No.: US 6,969,008 B2
(45) Date of Patent: Nov. 29, 2005

(54) POINT OF PURCHASE FRAGRANCE SAMPLING

(75) Inventors: Thomas A. Helf, New Berlin, WI (US); Edward J. Martens, III, Racine, WI (US); Scott D. Walter, Twin Lakes, WI (US); William D. Perez, Racine, WI (US); Thomas Jaworski, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 119 days.

(21) Appl. No.: 10/353,577

(22) Filed: Jan. 29, 2003

(65) Prior Publication Data

US 2004/0144853 A1 Jul. 29, 2004

(51) Int. Cl.[7] ........................................ A24F 25/00
(52) U.S. Cl. ........................ 239/4; 239/57; 239/102.1; 239/102.2; 239/34; 239/6; 222/180
(58) Field of Search ........................ 239/102.2, 102.1, 239/34–60, 4, 6; 222/180; 248/174, 309.1, 248/316.1; 229/159; 206/563

(56) References Cited

U.S. PATENT DOCUMENTS

| | | | |
|---|---|---|---|
| 3,043,523 A * | 7/1962 | Hogstrom | 239/274 |
| 3,844,057 A | 10/1974 | Johnson | |
| 4,085,893 A * | 4/1978 | Durley, III | 239/102.2 |
| 4,223,812 A * | 9/1980 | van Lit | 222/180 |
| 4,695,434 A | 9/1987 | Spector | |
| 4,702,418 A | 10/1987 | Carter et al. | |
| 4,869,407 A | 9/1989 | Booth, Jr. et al. | |
| 5,011,632 A | 4/1991 | Yano et al. | |
| 5,706,977 A * | 1/1998 | Ogura et al. | 221/197 |
| 5,724,957 A | 3/1998 | Rubsamen et al. | |
| 5,829,642 A | 11/1998 | Momboisse | |
| 5,950,619 A | 9/1999 | Van der Linden et al. | |
| 5,970,974 A | 10/1999 | Van Der Linden et al. | |
| 6,062,212 A * | 5/2000 | Davison et al. | 128/200.16 |
| 6,296,196 B1 | 10/2001 | Denen et al. | |
| 6,319,087 B1 | 11/2001 | Ferrigno | |
| 6,341,732 B1 * | 1/2002 | Martin et al. | 239/4 |
| 6,405,906 B1 | 6/2002 | De Laforcade | |
| 6,435,175 B1 | 8/2002 | Stenzler | |
| 6,439,474 B2 | 8/2002 | Denen | |
| 6,446,880 B1 | 9/2002 | Schram et al. | |
| 6,450,419 B1 | 9/2002 | Martens, III et al. | |
| 2002/0043568 A1 | 4/2002 | Hess et al. | |
| 2002/0106624 A1 | 8/2002 | Chan | |
| 2004/0146435 A1 | 7/2004 | Goldstein et al. | |

FOREIGN PATENT DOCUMENTS

FR 2 750 844 1/1998

OTHER PUBLICATIONS

Photograph of "Ambi Pur" fragrance dispenser taken prior to Oct. 8, 2002.

* cited by examiner

*Primary Examiner*—Dinh Q. Nguyen

(57) ABSTRACT

A fragrance sampling system for use in a store comprises a piezoelectrically vibrated orifice plate atomizer mounted to extend from a support structure in the store, such as a shelf and operated to emit puffs of very small droplets of the liquid fragrance and eject them upwardly into the atmosphere such that they become fully evaporated before contacting any supporting surface. The atomizer is controlled by electrical circuits which limit the times during which atomization occurs.

34 Claims, 11 Drawing Sheets

POINT OF PURCHASE FRAGRANCE SAMPLING

BACKGROUND OF THE INVENTION

1. Field of The Invention

This invention relates to fragrance sampling and more particularly it concerns novel methods and apparatus for ejecting atomized particles of a liquid fragrance in a manner to provide prospective customers at a point of purchase location, such as in a store, an accurate indication of a particular fragrance which they may wish to purchase.

2. Description of the Related Art

U.S. Pat. No. 6,450,419, No. 6,446,880, No. 6,439,474 and No. 6,296,196 disclose liquid fragrance dispensers which eject successive puffs of an atomized fragrance liquid into the atmosphere to condition the atmosphere in a room or other location. These devices use a piezoelectric actuator which is energized during successive intervals to vibrate an orifice plate. The orifice plate rests on the upper end of a wick which delivers liquid fragrance by capillary action from a reservoir to the underside of the vibrating orifice plate. When the plate vibrates, it converts the liquid into minute droplets and ejects these droplets into the atmosphere. The droplets evaporate as they fall back through the atmosphere and in this manner they condition the atmosphere. These vibrating orifice plate devices produce successive puffs of atomized liquid, each puff being approximately 11 milliseconds in length and the duration between successive puffs being adjustable over a range of nine to thirty six seconds. This has been found to provide good conditioning of the atmosphere in a room or other space in which the device is situated. Thus, vibratory plate atomizers can provide a pleasant fragrant ambiance in a room.

The above described dispensing devices have replaceable liquid fragrance reservoirs and accordingly many different fragrances can be dispensed by a particular device. Because of this it is necessary to provide at a point of purchase location, such as in a store, an arrangement which permits a customer to sample the fragrances in order to make a selection for purchase.

Several problems are involved in providing fragrance samples in the above. First, the sample must be emitted into the atmosphere in such a fashion that the prospective customer will receive an accurate portrayal of the fragrances as it will be experienced in the home. Secondly, the sample must be emitted in a manner such that only an appropriate amount of the liquid fragrance is used. Thirdly, the sample must be emitted in a manner that will not affect patrons or operations in nearby locations. In addition, the amount of liquid fragrance that is emitted must not be such that it would become deposited in liquid form on nearby surfaces which could result in corrosion of the surfaces or in causing the surfaces to become slippery and dangerous. Finally, the dispensed sample must be capable of rapid dispersal so that it will not interfere with subsequent or nearby sampling, or adjacent store operations.

Fragrance sampling devices are described in U.S. Pat. No. 3,844,057, No. 4,869,407, No. 5,829,642 and No. 6,405,906. According to U.S. Pat. No. 3,844,057, liquid fragrance is contained in pouches that are mounted on a flexible strip that is driven past a cutter knife. As the pouches pass by, the knife cuts them open so that the liquid fragrance drips out of the pouches onto an absorbent pad. A fan blows air through the pad to evaporate and disperse the liquid. According to U.S. Pat No. 4,869,407, a liquid fragrance contained in a porous wafer is sampled by squeezing a bellows which contains the wafer to force air through the wafer and into the atmosphere. According to U.S. Pat. No. 5,829,642, an aerosol device containing perfume or toilet water is mounted on the back side of a panel. A manual control means on the front of the panel can be pressed to actuate the aerosol device so that the contents thereof are ejected through a nozzle just above the control means. According to U.S. Pat. No. 6,405,906, a product receptacle is mounted inside an enclosure and is connected to be actuated by sliding an absorbent card into a slot in the enclosure. This causes liquid from the receptacle to be sprayed onto the absorbent card inside the enclosure. The card is then removed and the fragrance of the liquid can be sampled from the card.

U.S. Pat. No. 4,695,434, No. 4,702,418, No. 5,011,632, No. 5,724,957, No. 5,950,619 and No. 5,970,974, and U.S. Publication No. U.S. 2002/0043568 A1 U.S. Pat. No. 6,435,175, all describe liquid dispensing devices which have circuits or other means for controlling the timing of the dispensing operation.

U.S. Pat. No. 6,319,087 and U.S. Publication No. U.S. 2002/0106624 A1 describe the use of timing circuits in connection with point of purchase displays which do not involve the dispensing of a liquid fragrance.

None of the above patents provides the possibility of fragrance sampling which meets the criteria set forth above, namely sampling which accurately represents the effect of a vibratory plate atomizer, which experiences minimal liquid fragrance loss, and which avoids interference with subsequent or nearby sampling, or adjacent store operations.

SUMMARY OF THE INVENTION

The present invention provides point of purchase liquid fragrance sampling that gives prospective customers an accurate representation of the particular fragrance being sampled, while at the same time minimizing loss of the sampled fragrance and avoiding interference with nearby or subsequent sampling. The invention is based in part on the discovery that by positioning a vibrating plate atomizer at a location such that when a liquid fragrance sample is atomized, the atomized droplets will become fully evaporated without becoming deposited on nearby solid surfaces, accurate, efficient and unintrusive sampling can be achieved. The invention is based in further part on the discovery that the natural air currents at most point of purchase locations, such as in a store where sampling is usually carried out, will rapidly dissipate the fragrance and will avoid interference with subsequent or nearby fragrance sampling.

According to one aspect of the invention, there is provided a novel method of sampling a liquid fragrance which comprises the steps of atomizing a liquid fragrance from an atomizing device and ejecting atomized droplets of the atomized liquid fragrance from the device upwardly into the atmosphere; and, during the atomization, retaining the atomizing device on a platform while supporting the platform to extend outwardly from a support structure. In a preferred embodiment atomization of the liquid fragrance is carried out by vibrating an atomization plate while supplying the plate with the liquid fragrance so that the plate atomizes the liquid fragrance and ejects it into the atmosphere in the form of small liquid droplets which become fully evaporated without contacting the support structure.

According to another aspect of the invention, there is provided an air freshener sampling device which comprises a liquid fragrance atomizer, a platform on which the atomizer is securely retained and a mounting element secured to and extending between the platform and a support structure to mount the platform to extend outwardly from the support structure. In a preferred embodiment, a mounting element is secured to and extends from the platform. The platform is configured to be attached to a support structure in a manner such that said platform extends outwardly from said support structure.

DETAILED DESCRIPTION OF THE PREFERRED EMBODIMENTS

In the following, like reference numbers are used to identify similar elements in different embodiments.

Figure 1:
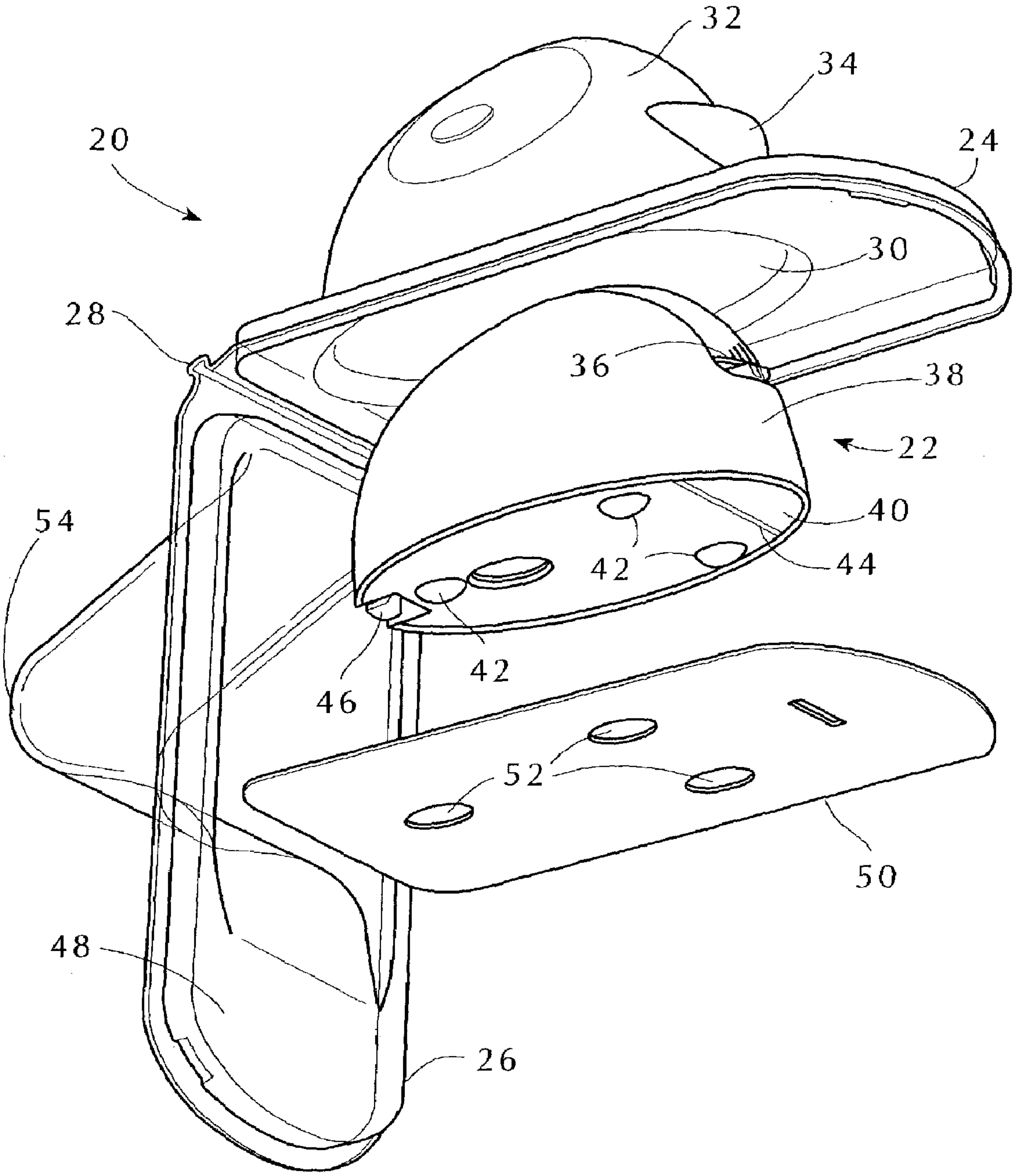
FIG. 1 is an exploded perspective view showing an atomizer and an enclosure, in opened condition, which forms a platform for securely retaining the atomizer and which can be mounted to extend out from a structure, in accordance with the present invention.

As shown in FIG. 1 a one piece enclosure shell 20 is provided to enclose an atomizer 22. The enclosure shell 20, which is shown in opened condition prior to enclosing the atomizer 22, comprises an upper platform portion 24 and a lower platform portion 26 which are joined at a hinge 28. The enclosure shell 20 may be made by thermoforming of any plastic material which is suitable for semi-rigid or rigid packaging, for example, polyvinyl chloride, high density polyethlyene, etc. The material of the enclosure shell 20 may be transparent so that a costumer who wishes to sample a fragrance will readily see the atomizer 22 from which the fragrance is being dispensed.

The upper platform portion 24 has a central opening 30 and is formed on its upper side with an atomizer enclosure formation 32 which surrounds the opening 30 and which closely accommodates the atomizer 22. Thus the atomizer enclosure formation 32 includes an adjustment switch protrusion 34 which accommodates an adjustment switch 36 that projects from an upper housing 38 of the atomizer 22.

The atomizer 22 has a flat base 40 which closes the bottom of the upper housing 38. Rounded feet 42 project downwardly from the base 40 so that when the atomizer is not enclosed within the enclosure shell 20, it may be supported on a surface, such as a table top. The base 40 is provided with a hinge 44 near one end to allow the base to be pulled downwardly to provide access to the interior of the atomizer 22. A latch 46 is formed at the other end of the base 40 to interlock with a latch holder (not shown) in the upper housing 38 of the atomizer 22 and hold the base 40 in closed position as shown.

The lower platform portion 26 of the enclosure shell 20 is formed with a shallow well 48 which accommodates a platform mounting template 50. The mounting template, which may be made of thin cardboard, is provided with openings 52 which accommodate the feet 42 on the base of the atomizer 22. In this manner the atomizer is held in a proper position with respect to the atomizer enclosure portion 32 of the enclosure shell 20. The lower platform portion 26 is also formed on its bottom side with a generally V-shaped mounting formation 54 which, as will be described more fully hereinafter, is used to support the enclosure shell 20 to extend out from a support member.

Figure 2:
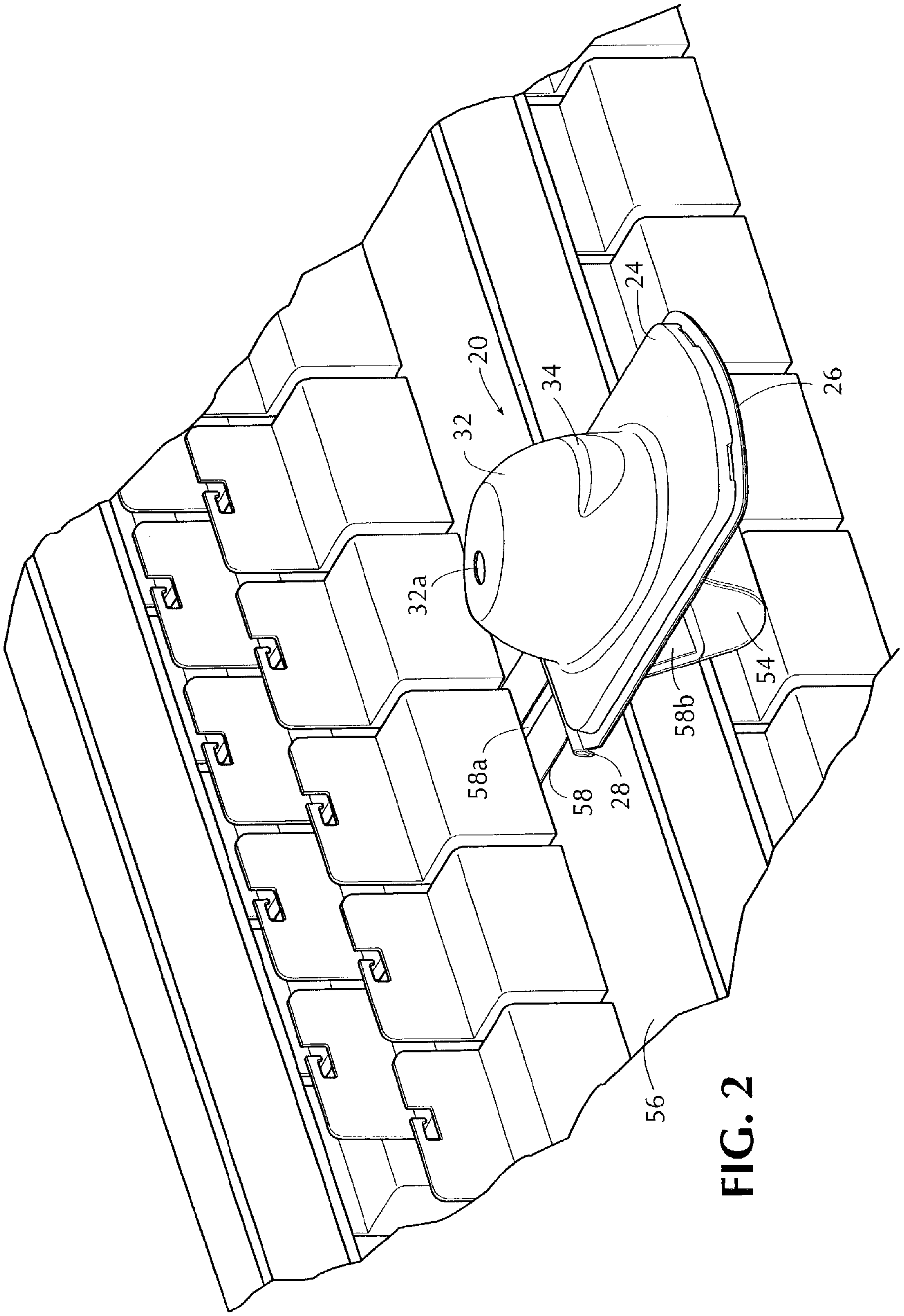
FIG. 2 is a perspective view of the enclosure of FIG. 1, in closed condition and extending out from an edge of a supporting shelf.

As can be appreciated from FIG. 1, the atomizer 22 can be inserted through the central opening 30 in the upper platform portion 24 and into the atomizer enclosure formation 32. Also, the platform mounting template 50 can be positioned in the well 48 on the lower platform portion 26. The upper and lower platform portions 24 and 26 may then be closed on each other via the hinge 28 to enclose the atomizer 22 as shown in FIG. 2. The platform portions 22 and 24 may be locked together, for example, by means of staples or welding, to restrict access to the atomizer 22.

Figure 3:
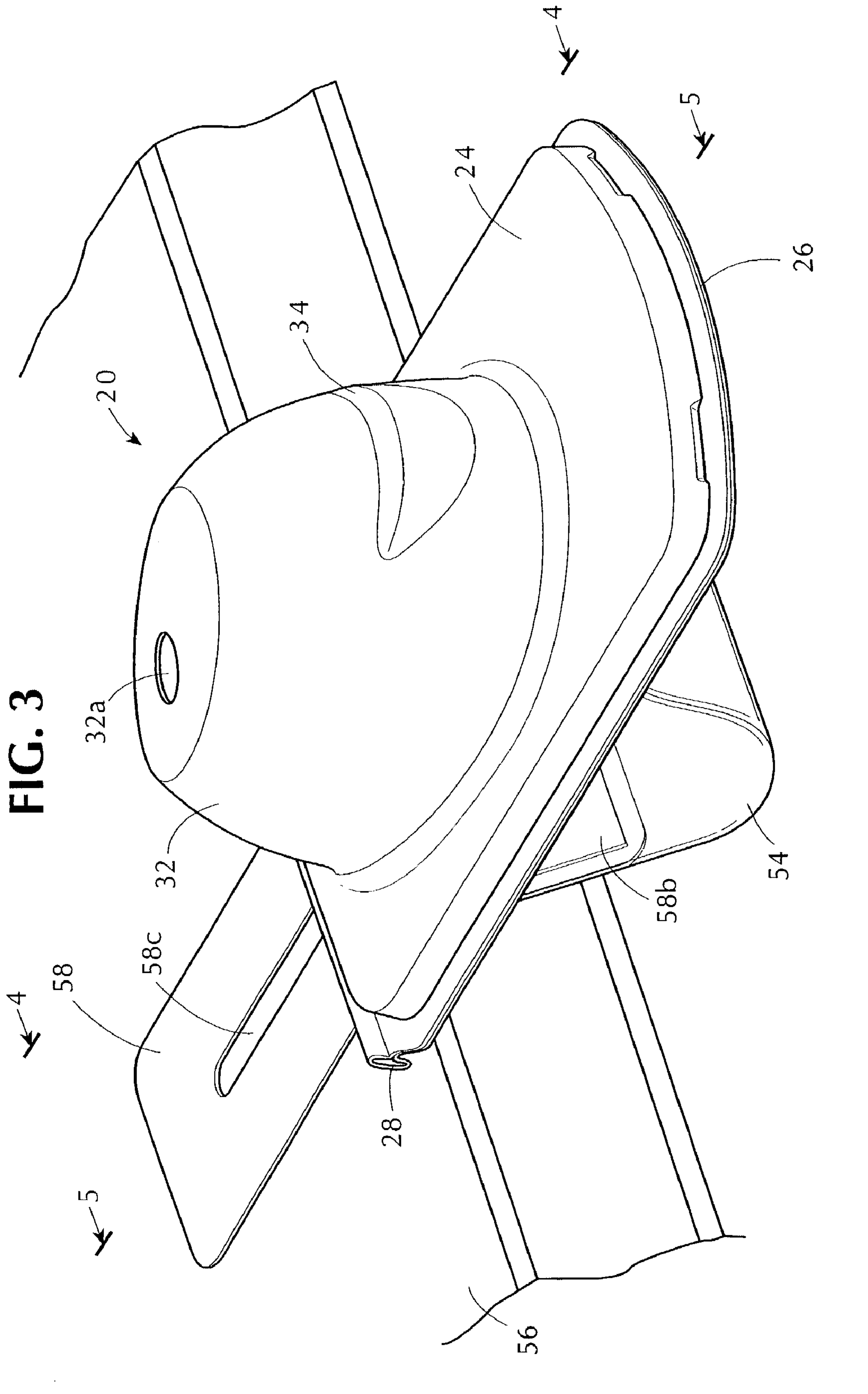
FIG. 3 is an enlarged perspective view showing the enclosure of FIG. 2 mounted on and extending out from the shelf of FIG. 2.
Figure 4:
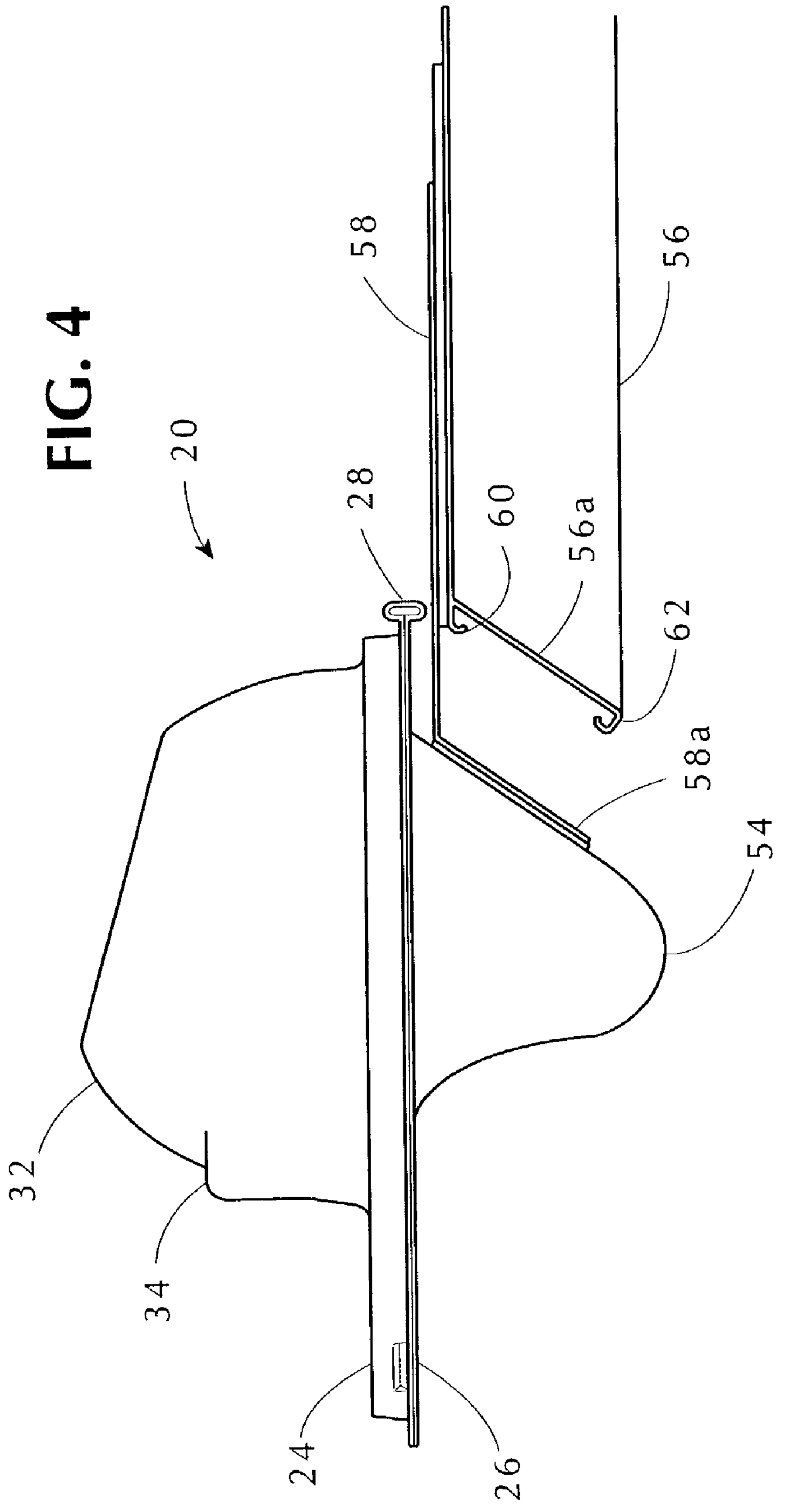
FIG. 4 is a side elevational view taken along line 4—4 of FIG. 2.

As can be seen in FIG. 2, the enclosure shell 20, with the atomizer 22 enclosed therein, is mounted to extend out from a support structure such as a shelf 56 at a point of purchase location in a store. The shelf 56 may be used to contain merchandise for sale, for example atomizers or replacement liquid reservoirs for such atomizers. Also, the shelf 56 may be part of a temporary display structure in the store which may be used to display replacement liquid fragrance reservoirs and/or liquid fragrance atomizers. In order to mount the enclosure shell 20 to extend out from the edge of the shelf 56, there is provided an enclosure mounting member 58 which is affixed to the shelf, for example by means of an adhesive. Alternatively, the mounting member 58 may be secured to the shelf 56 by means of a screw. For this purpose the mounting member is provided with a slot 58*a* to accommodate the screw. The configuration of the mounting member 58 is seen more clearly in the enlarged view of FIG. 3, and in the side view of FIG. 4. As seen in FIG. 4, the shelf 56 has a front edge 56*a*, which is slanted upwardly from bottom to top. Upper and lower shelf flanges 60 and 62 extend along the shelf front edge 56*a*. These flanges define recesses which can hold removable labels for indicating the price, etc. of merchandise located on the shelf. The mounting member 58 may be of any suitable material that will securely support the enclosure shell 20 and the atomizer 22. Preferably the mounting member 58 is a stainless steel plate having a thickness of about 0.020 inches (0.5 millimeters).

The mounting member 58 has an extension 58*b* which is bent downwardly beyond the edge of the support shelf 56 and which is adhesively fixed to a surface of the mounting formation 54 on the enclosure shell 20. In this manner the atomizer 22 is mounted in cantilever fashion to extend out from the shelf 56.

As can also be seen in FIG. 2, an atomizer enclosure ejection opening 32*a* is formed in the top of the atomizer enclosure formation 32. This opening is located in alignment with an atomizer ejection opening in the upper housing 38 of the atomizer 22. This permits atomized liquid, which is ejected upwardly from the atomizer 22, to pass though the atomizer enclosure formation 32 and up into the atmosphere.

Figure 5:
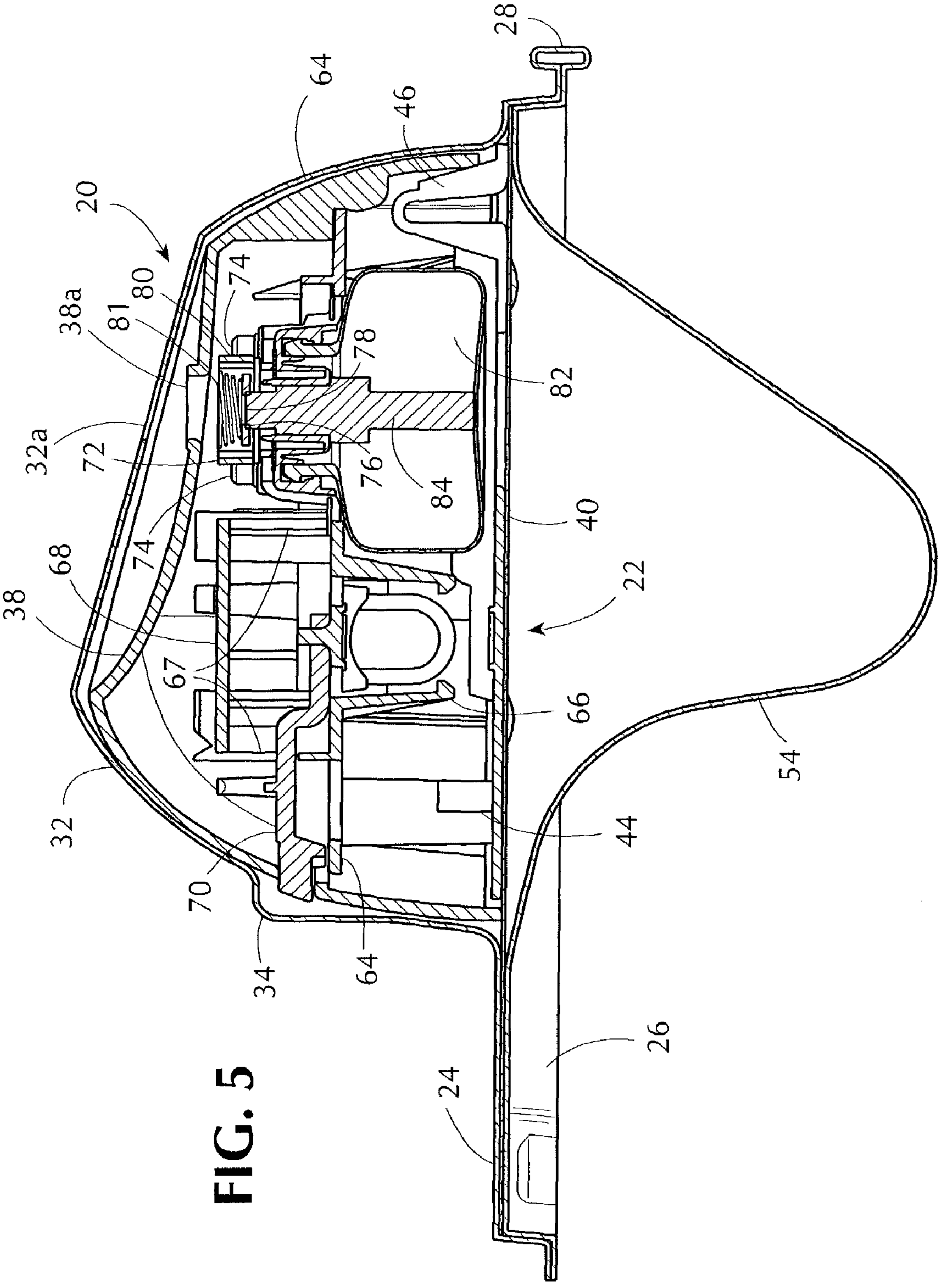
FIG. 5 is a section view taken along line 5—5 of FIG. 3.

The section view of FIG. 5 shows the general construction of the atomizer 22 which is contained within the atomizer enclosure formation 32. Preferably, the atomizer 22 is a piezoelectric type wherein an orifice plate is vibrated up and down at high frequency by means of a piezoelectric actuator element which is energized by alternating voltages applied across its upper and lower surfaces. This construction is similar to that shown and described in U.S. Pat. No. 6,450,419, the disclosure of which is incorporated by reference.

As can be seen in FIG. 5, a generally horizontal component support member 64 extends across the interior of the upper housing 38 of the atomizer. Battery retainer arms 66 extend downwardly from the support member 64 to hold a battery (not shown) for supplying electrical energy to the atomizer. Printed circuit support elements 67 extend upwardly from the support member 64 and mount a printed circuit board 68 which contains circuits for generating high frequency voltages at predetermined times and for controlling the duration of these voltages. An adjustment switch arm 70 is mounted on the support member 64 and is coupled to a switch (not shown) on the printed circuit board 68 for adjusting the predetermined times when the high frequency voltages are generated. The adjustment switch arm 70 extends out of the housing 38 so that it can be controlled when the atomizer is not used for fragrance sampling. However, when the atomizer 22 is enclosed within the enclosure shell 20, it is contained within the adjustment switch protrusion 34 and is not accessible for adjustment.

An atomizer pump assembly 72 is supported by posts 74 which extend upwardly from the support member 64. The pump and atomizer assembly comprises a flat annularly shaped piezoelectric actuator 76 and a thin orifice plate 78 which extends across the center opening of the actuator 76. The orifice plate is soldered or otherwise affixed to the actuator 76. When alternating electrical voltages are applied across opposite sides of the actuator 76, it expands and contracts accordingly in radial directions. This expansion and contraction causes the center opening of the actuator to become bigger and smaller, which in turn causes the center region of the orifice plate 78 to vibrate up and down.

The atomizer pump assembly 72 is contained within an atomizer pump assembly housing 80 which in turn is mounted on the posts 74. The housing 80 contains a coil spring 81 which presses down on the pump assembly 72.

A liquid fragrance reservoir 82 is releasably supported under the support member 64 below the pump assembly 72. The reservoir 82 is provided with a wick 84 which extends up from within the reservoir and out through an opening in the support member 64. The upper end of the wick 84 lightly touches the under side of the orifice plate 78 and supplies liquid by capillary action from the reservoir 82 to the orifice plate. Wires (not shown) from the printed circuit board 68 are connected to opposite sides of the piezoelectric actuator 76 to supply alternating voltages generated by the circuits on the printed circuit board to the actuator.

Vibration of the orifice plate 78 causes liquid fragrance, which is supplied to the plate from the reservoir 82, to be pumped through orifices in the plate and to be atomized and ejected upwardly from the plate to a height of about six to about eight inches (15–20 centimeters) above the atomizer 22. The upwardly ejected atomized liquid droplets pass up into the atmosphere through an atomizer housing ejection opening 38*a* and through an atomizer ejection opening 32*a*, both of which are located in alignment with the orifice plate. The droplets then become entrained in air currents above the atomizer and they evaporate before contacting any nearby supporting surfaces. The air into which the droplets become evaporated provides an accurate representation of the atmosphere in a room in which the atomizer 22 would normally be used. Thus a person in the vicinity of the atomizer 22 will be presented with an accurate representation of the fragrance being sampled. The diameters of the orifices in the orifice plate 78 are preferably between about 4 and about 5.5 microns.

The upwardly ejected atomized liquid fragrance comprises minute droplets which have a mean diameter between about five and about six microns; and 90% of the total volume of the droplets should comprise droplets having diameters less than eleven microns. These minute droplets become caught up in air currents passing over the enclosure shell 20 and are thereby quickly evaporated without becoming deposited in liquid form on any neighboring surfaces. Moreover the evaporated liquid fragrance is thereby presented in a form that is accurately representative of the fragrance as it would be dispensed during normal use of the piezoelectric atomizer. Thus with this arrangement a proper sampling of the liquid fragrance is achieved. In addition, the evaporated fragrance is readily dissipated so that it will not affect the atmosphere in nearby locations and also will not interfere with adjacent or subsequent fragrance sampling.

Figure 6:
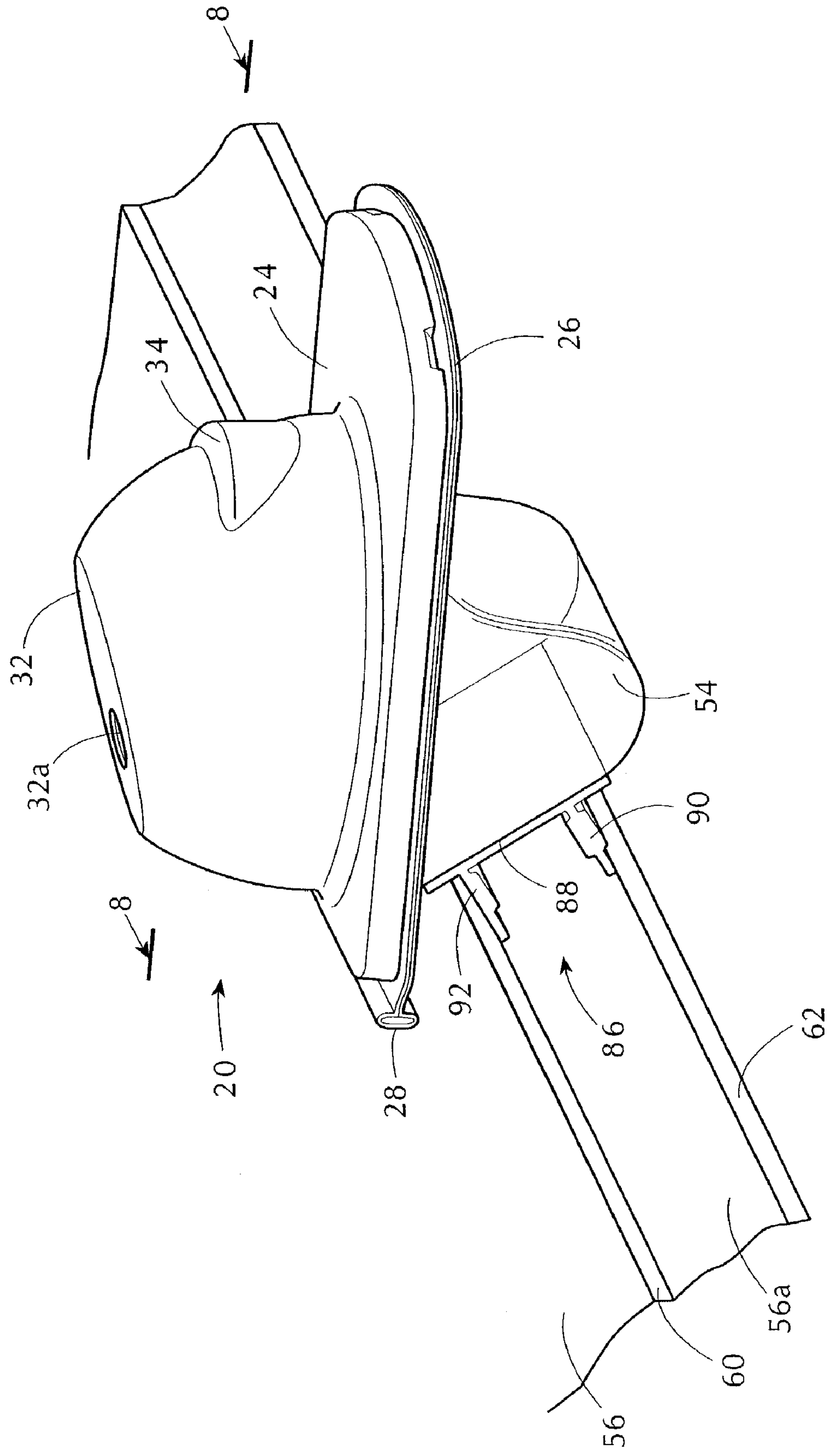
FIG. 6 is a view similar to FIG. 3 but showing an embodiment having an alternate mounting arrangement for the enclosure.
Figure 7:
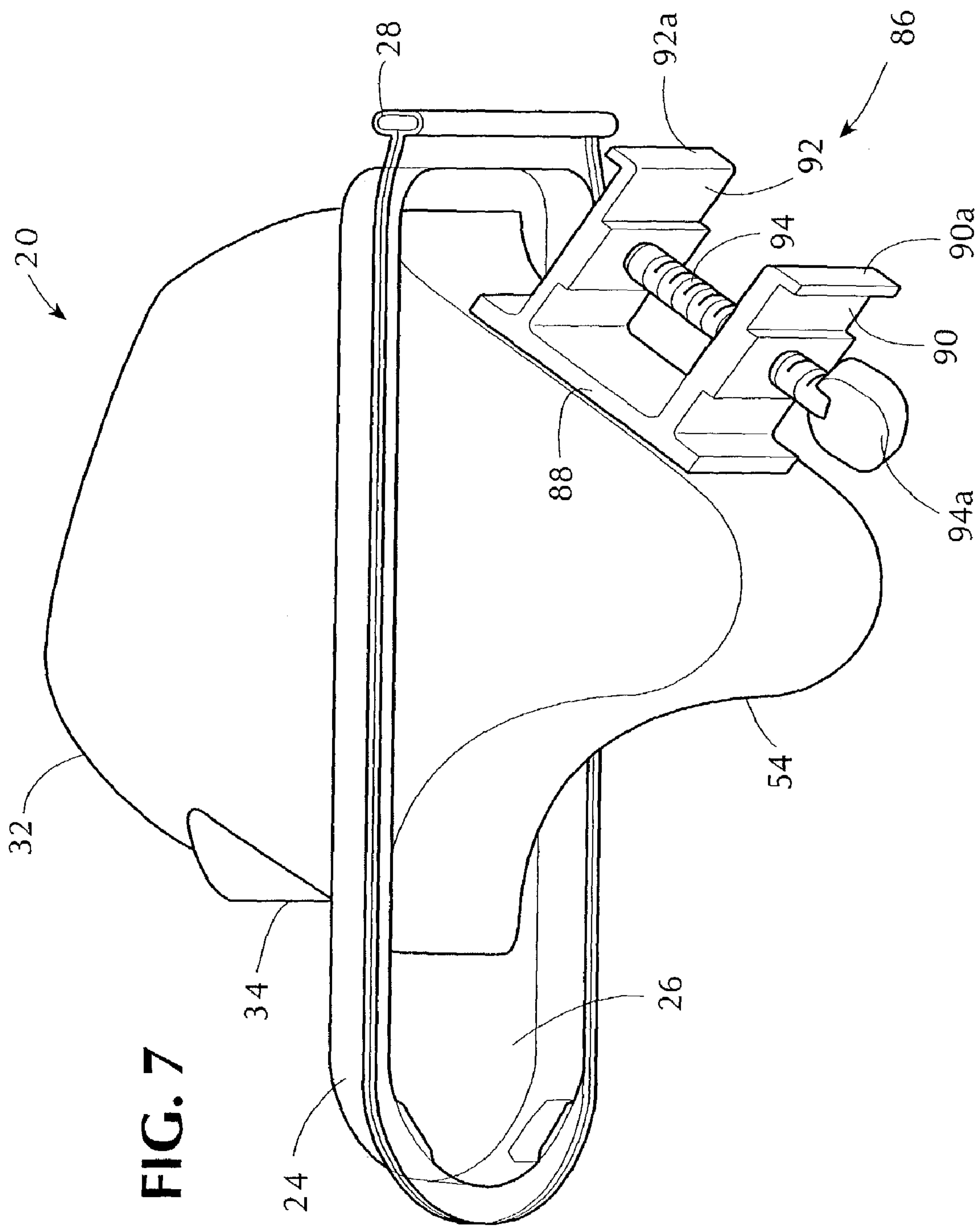
FIG. 7 is a reverse perspective view of the enclosure and alternate mounting arrangement of FIG. 6.
Figure 8:
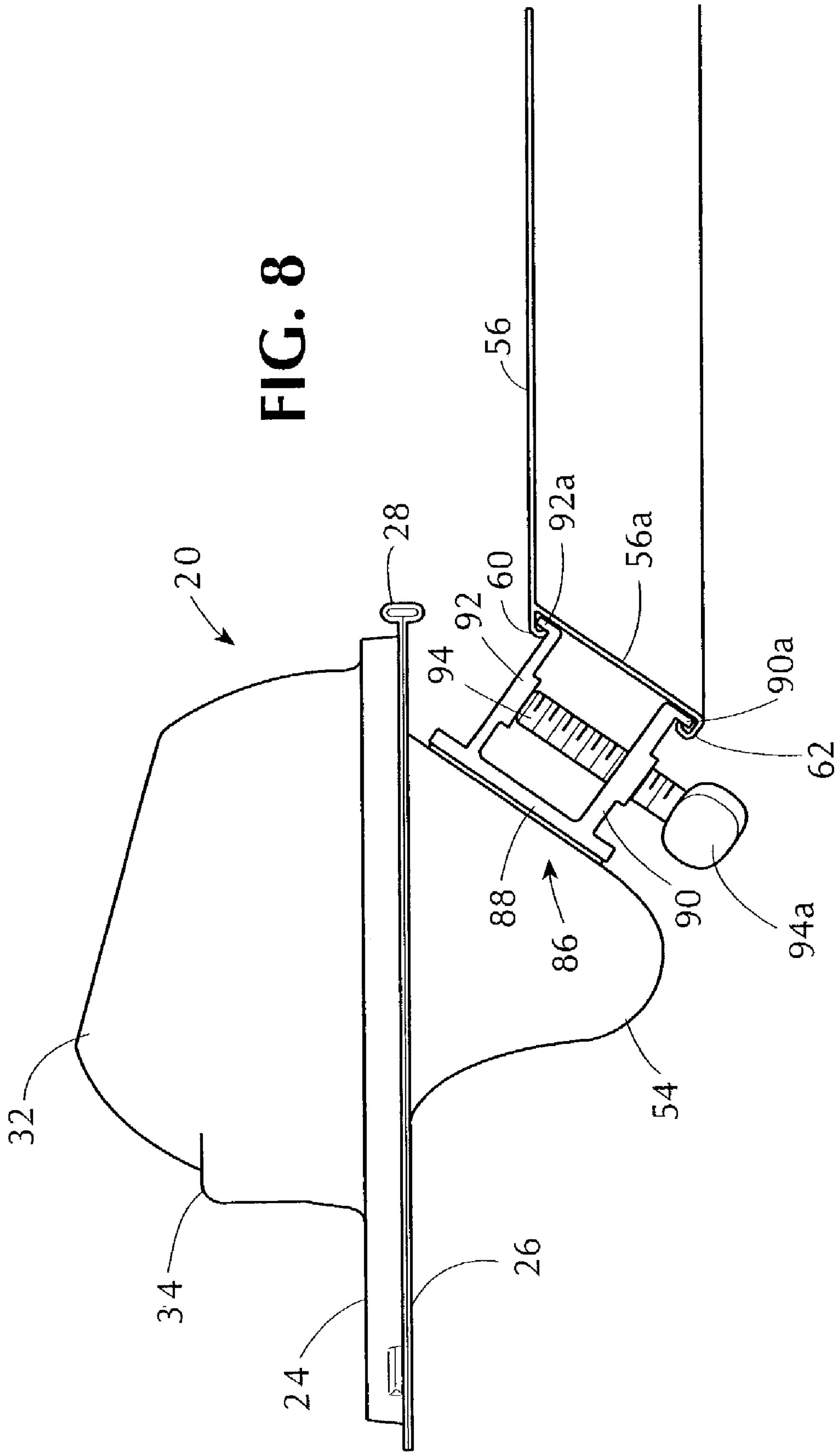
FIG. 8 is a view taken along line 8—8 of FIG. 6.

FIGS. 6, 7 and 8 show an embodiment in which the above described fragrance sampling system has an alternate mounting member 86 in place of the mounting member 58 of the preceding embodiment. The mounting member 86 comprises a flat base 88 from which extend first and second spreadable legs 90 and 92. The base 88 is adhesively attached to the mounting formation 54 on the lower platform portion 26. As shown in FIG. 7, a locking screw 94 is threaded through a hole in the first spreadable leg 90 and extends through the space between the legs so that its end presses against the second leg 92. By turning the screw 94, the legs 90 and 92 will become spread apart. While the locking screw 94 is shown with a flattened outer end 94*a* for easy turning, the screw may instead be provided with a formation that requires a special tool to turn it. This provides resistance to unauthorized removal of the sampling device.

The spreadable legs 90 and 92 have outwardly directed projections 90*a* and 92*a* at their outer ends. As can be seen in FIG. 8 these projections enter into recesses formed by the upper and lower shelf flanges 60 and 62 at the shelf front edge 56*a*. When the legs are spread apart by turning the screw 94, the projections 90*a* and 92*a* enter into and become locked in the recesses so that the mounting member 86 becomes secured to the shelf 56. Thus, the enclosure shell 20 and the atomizer 22 are held in a position extending outwardly from the shelf.

In the above embodiments, the atomizer 22 is free running and continuously emits puffs of fragrance for durations of about eleven milliseconds, which durations are separated by intervals of about nine seconds during which no fragrance is emitted. This has been found to provide a condition in the vicinity of the sampling device which accurately represents that provided by the atomizer when it is operating in a room; and yet the normal air currents in a store where the sampling device is used will quickly dissipate the fragrance so that it is not sensed in nearby locations in the store.

Figure 9:
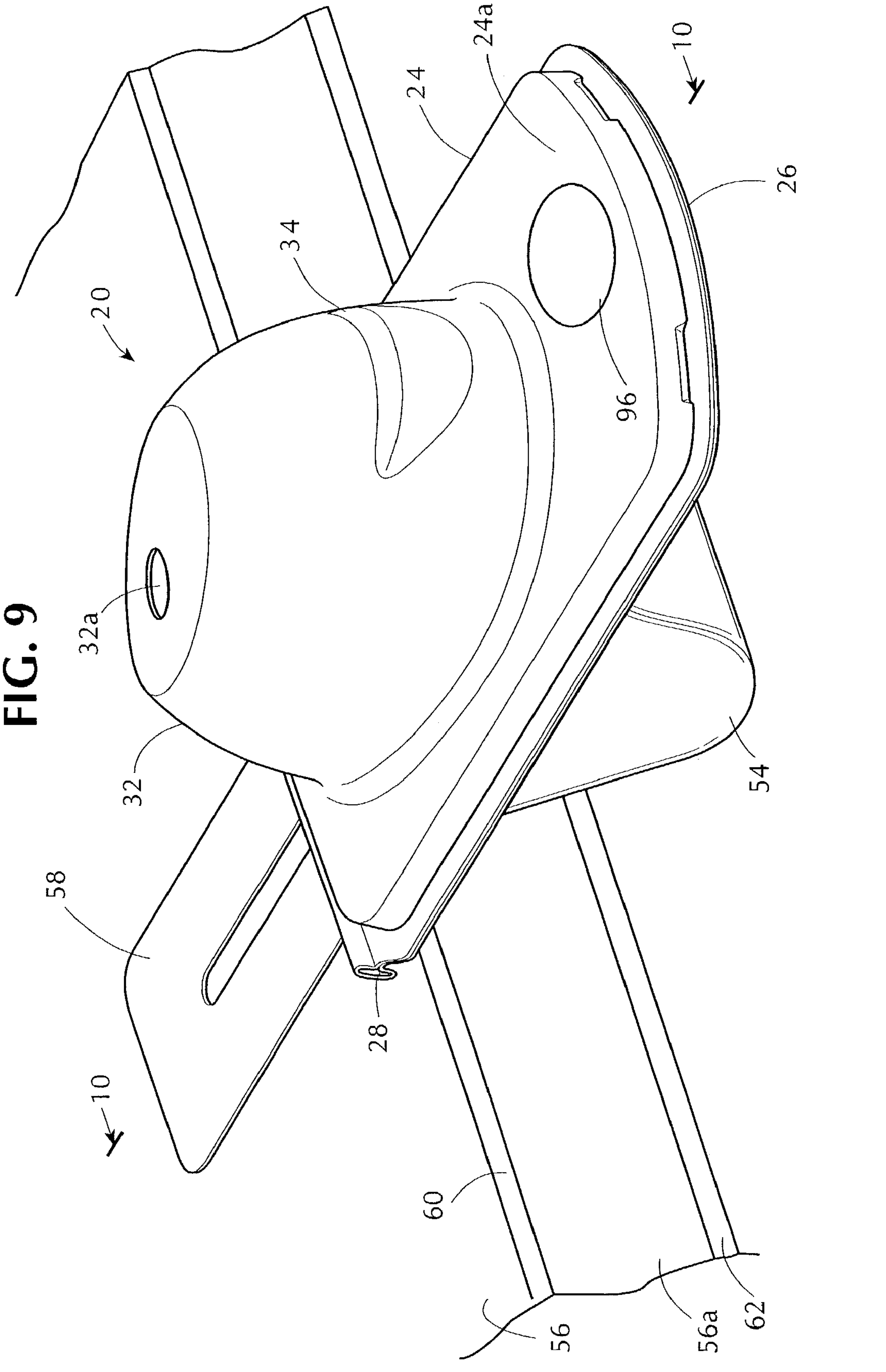
FIG. 9 is a perspective view similar to FIG. 3 and showing a further embodiment of the present invention.
Figure 10:
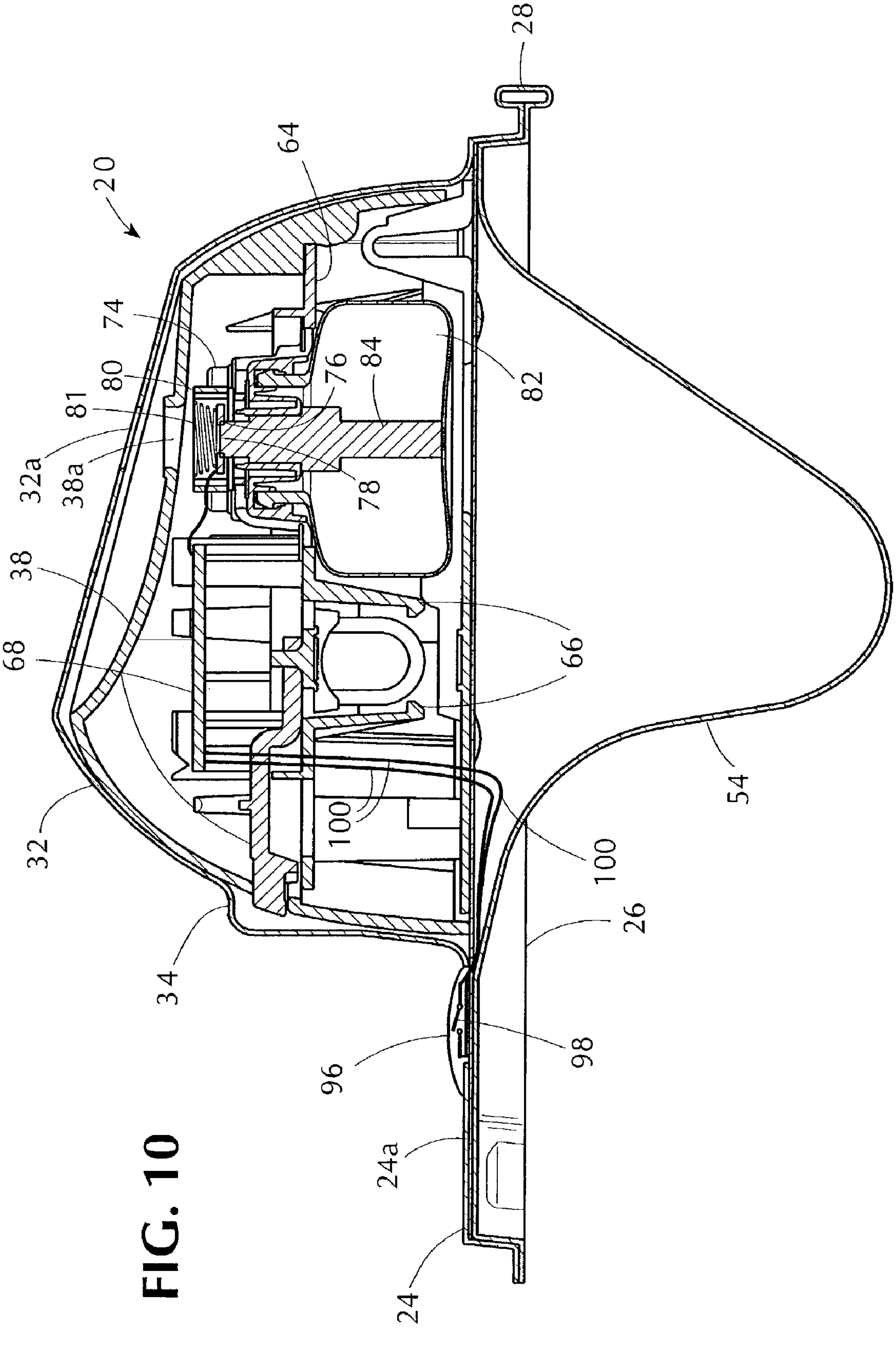
FIG. 10 is a view taken along line 10—10 of FIG. 9.
Figure 11:
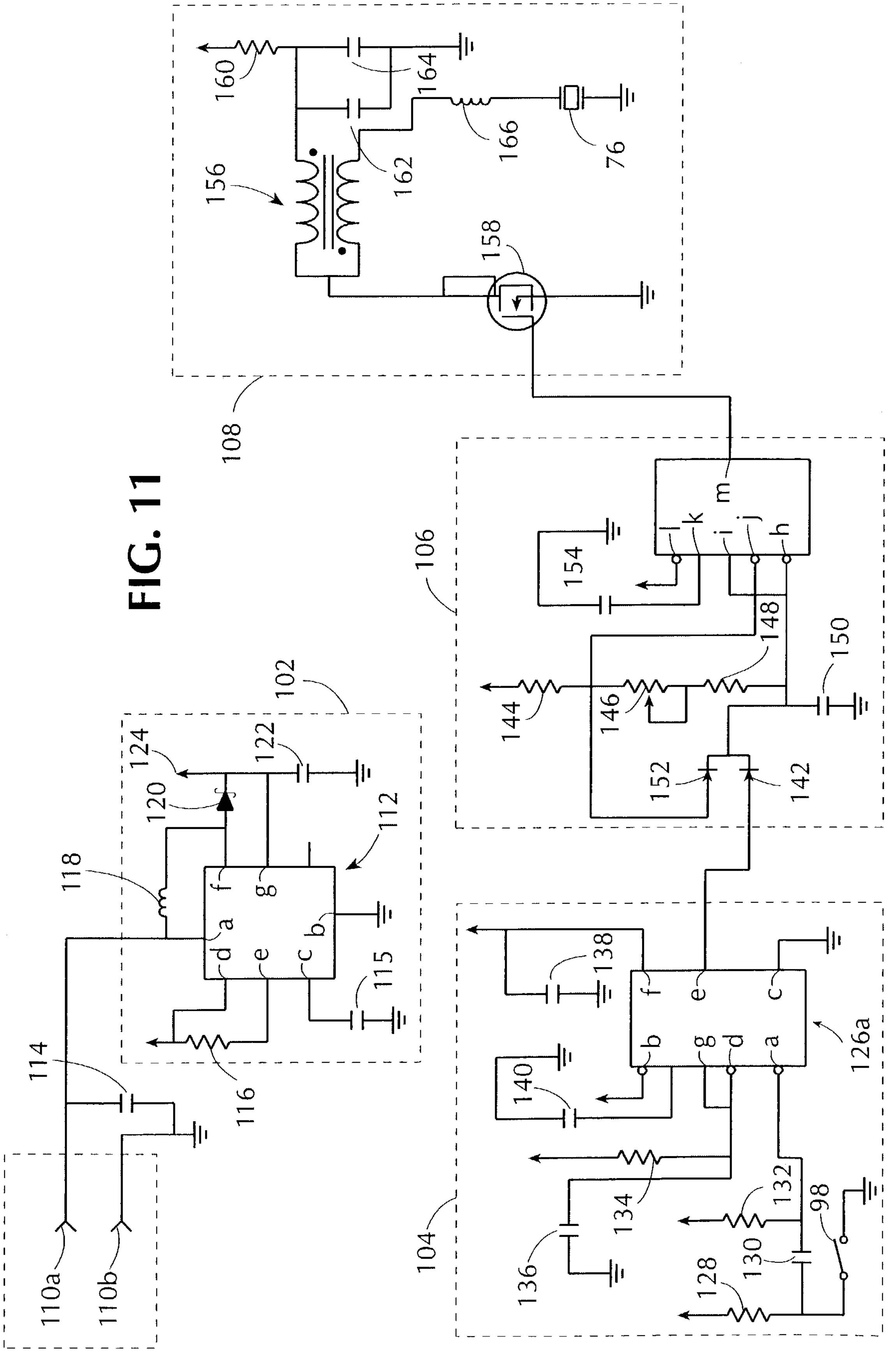
FIG. 11 is a circuit diagram for a circuit used in the embodiment of FIG. 9.

FIGS. 9, 10 and 11 show a still further embodiment of the invention wherein the sampling device is controlled by a person who wishes to sample a fragrance. In this embodiment there is provided a sampling button 96 on the upper platform portion 24 in front of the atomizer enclosure portion 24. This sampling button 96 operates a membrane switch 98 (FIG. 10) located under the upper platform portion. As can be seen in FIG. 10, the switch 98 is connected by a pair of switch wires 100 to the printed circuit board 68. The printed circuit board in this embodiment contains circuits which, when the switch 98 is closed in response to operation of the sampling button 96, cause the device to be actuated for a predetermined length of time, e.g. 15–20 milliseconds and to restrict the device from further actuation for another predetermined length of time, e.g. nine seconds. This ensures that a proper amount of liquid will become atomized for proper sampling; and that additional liquid will not be atomized before the initial sample has become dissipated.

FIG. 11 shows the circuits used in the circuit board 68 of the embodiment of FIGS. 9–11. Except for the sampling switch 98 and the piezoelectric actuator 76, all of the components shown in FIG. 11 are mounted on the printed circuit board 68. As shown in FIG. 11 these circuits and components are arranged to form a power supply 102, a one-shot generator 104, a drive frequency generator 106 and an actuator drive circuit 108. The power supply 102 operates to convert a 1.5 battery voltage input received via battery connections 110*a* and 110*b* to a 3.3 volt output on a system bus (indicated by arrowheads in the circuit diagram). This 3.3 volt output is supplied to the one-shot generator 104, the drive frequency generator 106 and the actuator drive circuit 108. The one-shot generator 104 operates to generate a low voltage output for a predetermined duration, e.g. 15 to 20 milliseconds whenever the sampling switch 98 in the one-shot generator 104 is closed. The drive frequency generator 106 operates to produce a high frequency (e.g. 140 kilohertz) square wave voltage output during the time that it receives the low voltage output from the one-shot generator 104. The actuator drive circuit 108 operates to increase the voltage of the high frequency signal received from the drive frequency generator 106 and to apply the increased voltage signal to the piezoelectric actuator element 76.

In the illustrative embodiment, the power supply 102 includes an integrated circuit in the form of a multi-purpose oscillator chip 112, for example a commercially available Maxim 756 IC (integrated circuit) single cell power supply chip. A battery voltage storage capacitor 114 is connected across the battery connections 110*a* and 110*b*. The positive voltage output from the battery terminals is applied to an input terminal a of the chip 112. A ground terminal b of the chip 112 is connected directly to ground; and a reference terminal c is connected through a capacitor 15 to ground. The 3.3 volt output from the power supply 102 is applied directly to a first power supply input terminal d and the 3.3 volt output is also applied via a control resistor 116 to a second power supply terminal e. A voltage booster coil 118 is connected between the input terminal a and an output terminal f of the chip 112. The chip 112 is arranged with an internal oscillator which alternately connects and disconnects the terminals f and b to and from each other. This causes the coil 118 to produce a high voltage at the terminal f. This high voltage is also applied via a rectifier diode 120 to one side of a power supply capacitor 122, the other side of which is connected to ground. The rectifier diode 120 prevents current from flowing from the power supply capacitor 122 back through the coil 118. As more and more current flows into the capacitor 122 from the coil 118, the voltage at the one side of the capacitor increases. This voltage is applied to an output terminal 124 which is connected to a bus (not shown) from which the other components obtain their 3.3 volt operating voltage (shown as upwardly pointing arrows in FIG. 11). The voltage output of the capacitor 122 is also applied to a cutoff terminal g of the chip 112; and, when that voltage exceeds 3.3 volts, the oscillator function of the integrated circuit stops. Thereafter, when the voltage at the terminal g drops below 3.3 volts, the oscillator operation is restarted so that the coil 118 operates to re-build the voltage output of the output terminal 124.

As indicated above, the one-shot generator 104 operates to produce an output actuation signal in the form of a decreased output voltage when the sample ejection button 96 is pressed to close the sampling switch 98; and to maintain this actuation signal for a predetermined duration, e.g. 15–20 milliseconds. The one-shot generator 104 may be formed from one half 126*a* of a commercially available integrated circuit chip 126, such as one half of a Texas Instruments 556 timer chip. The sampling switch 98 is arranged on a front ledge 24*a* of the upper support platform 24 (FIG. 1) to be operated by the sampling button 96. The switch 98 as shown in FIG. 11, is connected on one side to ground potential and, on the other side, through a trigger resistor 128, to the 3.3 volt bus from the power supply circuit 102. A trigger capacitor 130 is connected on one side to a junction between the switch 98 and the resistor 128. The other side of the trigger capacitor 130 is connected through a reset resistor 132 to the 3.3 volt bus. The junction between the reset resistor 132 and the trigger capacitor 128 is connected to a trigger input terminal a of the chip 126. A power input terminal b of the chip is connected to the 3.3 volt bus and a ground terminal c of the chip is connected to ground. The one-shot generator 104 also includes a timing circuit which comprises a one shot timing resistor 134 and a timing capacitor 136 connected in series between the 3.3 volt bus and ground. The junction between the resistor 134 and the capacitor 136 is connected to a hold terminal d of the chip 126.

When the sampling switch 98 is closed, the voltage at the junction between the trigger resistor 128 and the trigger capacitor 130 decreases momentarily, until the trigger capacitor recharges through the reset resistor 128. This decrease in voltage, which is applied to the trigger input terminal a of the chip 126, causes the voltage at the hold terminal d to drop and discharge the timing capacitor 136. This voltage drop also appears at an output terminal e of the chip 126. The voltage drop remains irrespective of a rising voltage at the trigger input terminal a caused by recharging of the trigger capacitor 130 through the reset resistor 132. The voltage drop at the hold terminal d of the chip 126 remains until the timing capacitor 136 recharges through the timing resistor 134, which is set for a duration of about 15 to 20 milliseconds. When the timing capacitor 136 recharges, the voltage applied to the hold terminal d becomes large enough to cause the chip to increase the voltage output at its output terminal e. The chip 126 also includes a first decoupling terminal f which is connected through a first decoupling capacitor 138 to ground and a second decoupling terminal g which is connected to the 3.3 volt bus and to a second decoupling capacitor 140 to ground. The decoupling capacitors 138 and 140 allow discharge of high frequencies which may be produced during operation of the device so that these frequencies do not appear in the power supply 102.

The 15 to 20 millisecond time constant of the one shot generator 104 is considered to be an appropriate duration for atomization to take place upon pushing the sample ejection button 96 so that the output of the atomizer 22 will provide an accurate representation of the atmosphere in a room which would be conditioned by the fragrance.

As mentioned above, the drive frequency generator 106 operates, while being supplied with a low voltage from the one-shot generator 104, to produce a high frequency (e.g. 145 kilohertz) square wave output. The high frequency generator 106 may be formed from a second half 126*b* of the integrated circuit chip 126 of the one-shot generator 104. The voltage from the one-shot generator 104 is applied via a first input diode 142 to a one-shot input terminal h of the chip 126. A frequency control circuit, comprising first, second and third frequency control resistors 144, 146 and 148 in series with a frequency control capacitor 150, is connected between the 3.3 volt bus and ground. The junction between the capacitor 150 and the resistor 148 is connected to the one-shot input terminal 126*h* as well as to a feedback terminal i of the chip 126. In addition, a feedback terminal j of the chip 126 is connected to the junction between the frequency control resistors 144 and 146. This junction is also connected via a second input diode 152 to the junction between the frequency control capacitor 150 and the third frequency control resistor 148. The second frequency control resistor 146 is constructed as a variable potentiometer to provide for frequency adjustment. A decoupling capacitor 154 is connected between a decoupling terminal k of the chip 126 and ground to decouple any noise that is produced during operation of the device from the power supply 102. Finally, 3.3 volt power is applied from the 3.3 volt bus to a voltage input terminal l of the chip 126.

The above-described circuit operates to produce a square wave voltage output at a high frequency output terminal m of the chip 126. The output frequency can be varied by adjusting the setting of the second frequency control resistor 146. The square wave output at the terminal m is not symmetrical but instead it has a duty cycle such that the voltage is high for one third of a cycle and is low for the remaining two thirds of the cycle.

The actuator drive circuit 108, as mentioned above, causes the piezoelectric actuator 76 to expand and contract radially at the output frequency of the drive frequency generator 106. The actuator drive circuit 108 comprises a transformer 156 the coils of which are connected together at one end. The junction between the coils of the transformer 156 is connected through the source and drain of a field effect transistor 158 to ground. The high frequency output terminal 126*m* of the chip 126 in the drive frequency generator 106 is connected to the gate terminal of the field effect transistor 158.

One end of the transformer 156 is connected to the junction between a charge accumulation resistor 160 and a pair of charge accumulation capacitors 162 and 164 which are connected in parallel with each other between the charge accumulation resistor 160 and ground. The other end of the transformer 156 is connected via a smoothing coil 166 to one side of the piezoelectric actuator 76. The other side of the actuator 76 is connected to ground.

The high frequency square wave voltage from the drive frequency generator 106 which is applied to the gate of the field effect transistor 158 causes the transistor to become conductive and non-conductive alternately at the frequency of the drive frequency generator. This in turn causes the voltage at the one end of the transformer 156 to go high and low at the same frequency but at a much higher voltage, e.g. 180 volts peak to peak. This high frequency alternating voltage is applied across the piezoelectric actuator 76, causing it to expand and contract at the same frequency.

The resistance value of the charge accumulation resistor 160 and the capacitance values of the charge accumulation capacitors 162 and 164 are chosen such that during the time that the field effect transistor is rendered alternately conductive and non-conductive the charge accumulation capacitors 162 and 164 gradually lose their charge. The charge accumulation resistance and capacitance values are set such that after a period of about 15 to 20 milliseconds the charge at the junction between the transformer coils is too low to further drive the piezoelectric actuator element 76; and the charge does not build itself up again via the charge accumulation resistor 160 for about 9 seconds. These timing values may vary according to the particular fragrance being dispensed and the characteristics of the atomizer 22.

The significance of the timing provided by the charge accumulation resistor 160 and the charge accumulation capacitors 162 and 164 is that it limits the operation of the device such that whenever the sample ejection button 96 is pressed the device will produce a continuous atomization of liquid for a period of 15 to 20 milliseconds irrespective of whether the button is pushed again within the next nine seconds. This allows a proper amount of fragrance to be ejected into the surrounding atmosphere for obtaining an accurate indication of the fragrance. At the same time it avoids the ejection of an overabundance of the fragrance, which could interfere with its proper presentation to a customer and which could too rapidly deplete the fragrance from the reservoir 82. Further, this timing arrangement allows the atmosphere in the vicinity of the atomizer 22 to become cleared before a new sample is presented.

INDUSTRIAL APPLICABILITY

The above described device makes it possible to project a sample of a fragrance into the atmosphere at a sampling station in a store in a manner such that the atmosphere becomes conditioned to accurately simulate the effect that would be produced by the ejection of the fragrance in successive puffs without affecting the atmosphere in nearby locations in the store.

What is claimed is:

1. A method of sampling a fragrance comprising the steps of:

atomizing a liquid fragrance from an atomizing device having a housing, and ejecting atomized droplets of the atomized liquid fragrance from within the device upwardly through a housing aperture in the housing into the atmosphere;

during said atomization, retaining said atomizing device on a platform and within an enclosure having an enclosure aperture; and supporting the platform with an arm, such that the platform extends outwardly from a support structure, wherein said atomization step of atomizing the liquid fragrance and ejecting atomized droplets includes ejecting the atomized droplet from within the enclosure upwardly through the enclosure aperture.

2. A method of sampling a liquid fragrance according to claim 1 wherein, said step of atomization comprises vibrating an atomization plate while supplying the plate with the liquid fragrance so that the plate atomizes the liquid fragrance and ejects it into the atmosphere in the form of small liquid droplets which become fully evaporated without contacting said support structure.

3. A method of sampling a liquid fragrance according to claim 2 wherein, the droplets have particle sizes in the range of about five to about six microns and wherein at least 90% of the volume of the droplets is made up of droplets having a particle size less than eleven microns.

4. A method according to claim 1 wherein, said sampling is carried out at a point of purchase location.

5. A method according to claim 1, wherein the platform has a V-shaped mounting formation, by which the platform is mounted on an arm which is affixed to and extends out from said support structure.

6. A method according to claim 5 wherein, the support structure is a shelf in a store.

7. A method according to claim 1 wherein, the atomization plate is vibrated for a duration of about fifteen to about twenty milliseconds following the operation of a sampling switch which is connected to initiate said atomization.

8. A method according to claim 7 wherein, the sampling switch is connected to be rendered ineffective to initiate significant vibration of the atomization plate for a duration of at least nine seconds following prior initiation of vibration.

9. A method according to claim 1 wherein, the atomization plate is vibrated repeatedly for periods of about eleven milliseconds which periods are interspersed with rest periods of about nine seconds.

10. A method according to claim 1 wherein, the atomization plate is prevented from substantial vibration for a period of at least nine seconds following a previous vibration thereof.

11. A method according to claim 10, wherein the droplets are ejected upwardly in the atmosphere to a height of about six to about eight inches above the atomizing device.

12. A fragrance sampling device comprising:

an atomizer for atomizing a liquid fragrance and for ejecting atomized droplets of the atomized liquid fragrance upwardly into the atmosphere, said atomizer being housed in an atomizer housing, said atomizer housing having a housing aperture such that the droplets of the atomized liquid fragrance are ejected within the housing and upwardly through the housing aperture;

a platform on which said atomizer housing is securely retained;

an enclosure in which said atomizer is enclosed when mounted on said platform, said enclosure having an enclosure opening such that the droplets are ejected from within the enclosure upwardly through the enclosure aperture; and a mounting element secured to and extending from said platform, said mounting element being configured to be attached to a support structure in a manner such that said platform extends outwardly from said support structure.

13. A fragrance sampling device according to claim 12, wherein said atomizer comprises:

a vibratory atomization plate;

a liquid reservoir for containing a liquid fragrance to be sampled;

a liquid delivery system for delivering liquid from said reservoir to said atomization plate to be atomized thereby and ejected into the atmosphere in the form of small liquid droplets; and a piezoelectric vibration device connected to vibrate said atomization plate.

14. A fragrance sampling device according to claim 13 wherein, said mounting element comprises a cantilever mounting arm.

15. A fragrance sampling device according to claim 13 wherein, said mounting element comprises a bracket which can be fastened to a shelf.

16. A fragrance sampling device according to claim 15 wherein, said bracket is a metal strip that is adhesively attached to said platform and that can extend over and become affixed to a shelf.

17. A fragrance sampling device according to claim 15 wherein, said bracket includes a base that is adhesively attached to said platform and which has a pair of legs that are spreadable by means of a screw to become forced between projections along the edge of a shelf.

18. A fragrance sampling device according to claim 13 wherein, said atomization plate comprises an orifice plate formed with a plurality of orifices in the range of about four to about five and a half microns in diameter.

19. A fragrance sampling device according to claim 18 wherein, said liquid delivery system comprises a wick extending from said reservoir to a location under said orifice plate.

20. A fragrance sampling device according to claim 19 wherein, said liquid reservoir is located under said orifice plate and wherein said wick extends from within said reservoir to the underside of said orifice plate.

21. A fragrance sampling device according to claim 13 wherein, said atomizer plate comprises an orifice plate formed with a plurality of orifices and which is configured and operated to generate a plurality of liquid droplets having an average particle diameter in the range of about five to about six microns and wherein 90% of the total volume of said droplets is made up of droplets whose particle size is less than eleven microns.

22. A fragrance sampling device according to claim 21 wherein, said atomizer is constructed to eject said droplets to a height of about six to about eight inches above said atomizer.

23. A fragrance sampling device according to claim 21 wherein, said atomizer includes a piezoelectric actuator element coupled to said orifice plate to vibrate same upon energization of said actuator element, and wherein said atomizer further includes an electric circuit which is configured to supply alternating high frequencies across said actuator element.

24. A fragrance sampling device according to claim 23 wherein, said sampling switch is positioned on said platform at a location across from said mounting element.

25. A fragrance sampling device according to claim 21, wherein said electric circuit is configured to energize said piezoelectric actuator element for periods of about eleven milliseconds which are interspersed by periods of non-energization of at least nine seconds.

26. A fragrance sampling device according to claim 25 wherein, said electric circuit is configured to prevent substantial subsequent energization of said actuator element for a period of at least nine seconds following a previous energization of said actuator element.

27. A fragrance sampling device according to claim 21, wherein said electric circuit includes a manually operable sampling switch which is connected to initiate energization of said actuator element.

28. A fragrance sampling device according to claim 27 wherein, said electric circuit is configured to energize said actuator element for a period of about fifteen to about twenty milliseconds following operation of said sampling switch.

29. A fragrance sampling device according to claim 28 wherein, said sampling switch is a membrane switch.

30. A fragrance sampling device according to claim 12 wherein, said enclosure has a clamshell configuration and which can be opened to accommodate said atomization device and which can be closed to enclose said atomization device, and a substantially V-shaped mounting formation to which said mounting element is secured.

31. A fragrance sampling device according to claim 30 wherein, said enclosure is lockable in its closed condition.

32. A fragrance sampling device according to claim 31 wherein, said enclosure is locked in closed condition enclosing said atomization device by means of staples which extend through flanges around the periphery of said atomization device.

33. A fragrance sampling device according to claim 12 wherein, said enclosure is transparent.

34. An apparatus comprising:

an atomizer for atomizing a liquid fragrance and for ejecting atomized droplets of the atomized liquid fragrance, said atomizer being housed within a housing having a base and an upper cover, said upper cover of said housing having a housing aperture such that the atomized droplets of the atomized liquid fragrance are ejected within the housing and upwardly through the housing aperture;

a shell substantially enclosing said housing of said atomizer, said shell comprising an upper platform and a lower platform, said upper platform of said shell having a shell aperture substantially aligned with said housing aperture, through which the atomized droplets of the atomized liquid fragrance can be ejected from below said upper platform, said lower platform supporting said base of said housing;

a mounting element secured to and extending from said shell, for supporting said shell with said atomizer therein; and a support structure, said mounting element being coupled to said support structure, so as to support said atomizer spaced a distance from said support structure.

* * * * *

UNITED STATES PATENT AND TRADEMARK OFFICE

CERTIFICATE OF CORRECTION

PATENT NO. : 6,969,008 B2
APPLICATION NO. : 10/353577
DATED : November 29, 2005
INVENTOR(S) : Thomas A. Helf et al.

It is certified that error appears in the above-identified patent and that said Letters Patent is hereby corrected as shown below:

Column 11: Line 2, after “a” add --substantially--

Column 11: Line 11, after “atomization” add --step--

Column 14: Line 11, replace “ejeected” with --ejected--

Signed and Sealed this

Twelfth Day of August, 2008

JON W. DUDAS
*Director of the United States Patent and Trademark Office*